US009526826B2

(12) United States Patent
Nagar et al.

(10) Patent No.: US 9,526,826 B2
(45) Date of Patent: Dec. 27, 2016

(54) INFUSION SET WITH QUICK CONNECT, SELF-ALIGNED ELECTRICAL CONTACTS

(75) Inventors: Ron Nagar, Tel Aviv-Jaffa (IL); Gabriel Bitton, Jerusalem (IL); Elisha Amir, Livnim (IL)

(73) Assignee: INSULINE MEDICAL LTD., Petach-Tikva (IL)

( * ) Notice: Subject to any disclaimer, the term of this patent is extended or adjusted under 35 U.S.C. 154(b) by 306 days.

(21) Appl. No.: 14/117,270

(22) PCT Filed: May 16, 2012

(86) PCT No.: PCT/IL2012/000194
§ 371 (c)(1),
(2), (4) Date: Jul. 30, 2014

(87) PCT Pub. No.: WO2012/156967
PCT Pub. Date: Nov. 22, 2012

(65) Prior Publication Data
US 2014/0336579 A1    Nov. 13, 2014

Related U.S. Application Data (60) Provisional application No. 61/486,534, filed on May 16, 2011.

(51) Int. Cl.
*A61M 39/10* (2006.01)
*A61M 5/14* (2006.01)
*H01R 13/00* (2006.01)

(52) U.S. Cl.
CPC ........... *A61M 5/1413* (2013.01); *A61M 39/10* (2013.01); *H01R 13/005* (2013.01); *A61M 2039/1022* (2013.01); *A61M 2039/1077* (2013.01)

(58) Field of Classification Search
CPC .................... A61M 2039/1022; A61M 39/10; A61M 2039/1005; A61M 2039/265; H01R 13/005
See application file for complete search history.

(56) References Cited

U.S. PATENT DOCUMENTS

| 3,452,366 A | 7/1969 | Downey |
| 8,915,879 B2 * | 12/2014 | Smith .................. A61M 5/145 604/152 |

FOREIGN PATENT DOCUMENTS

| WO | WO 2008/137813 A1 | 11/2008 |
| WO | WO 2012/022771 A2 | 2/2012 |

OTHER PUBLICATIONS

International Search Report of PCT/IL2012/000194 issued on Dec. 12, 2012.

* cited by examiner

*Primary Examiner* — Kevin C Sirmons
*Assistant Examiner* — Deanna K Hall
(74) *Attorney, Agent, or Firm* — Cooley LLP (57) ABSTRACT

A device and method for delivering a therapeutic substance to the body of a mammal may include a pump adapter, a pump, and an infusion set having a distal connector and a proximal connector. The proximal connector and the pump adapter have connecting electrical contacts which can be connected to one another in a single action when the proximal connector and pump are being secured to the pump adapter. The distal connector of the infusion set can be connected to a catheter housing, which can be secured to the mammal's skin. The distal connector and the catheter housing have additional connecting electrical contacts which can be connected to one another in a single action when connecting the distal connector to the catheter housing.

20 Claims, 5 Drawing Sheets

INFUSION SET WITH QUICK CONNECT, SELF-ALIGNED ELECTRICAL CONTACTS

CROSS-REFERENCE TO RELATED APPLICATION

The present application claims priority to International Patent Application No. PCT/IL2012/000194, to Ron Nagar et al., filed May 16, 2012, and entitled "INFUSION SET WITH QUICK CONNECT, SELF-ALIGNED ELECTRICAL, CONTACTS", which claims priority to U.S. Provisional Patent Application No. 61/486,534, filed on May 16, 2011, the disclosures of which are incorporated herein by reference in their entireties.

TECHNICAL FIELD

The subject matter described herein relates generally to systems and methods for delivering one or more drugs to a user while applying treatment to the infused drug site. In particular, the subject matter described herein relates to systems and methods for subcutaneous injection of a medicament using a regular drug infusion pump and an improved infusion set that includes one or more treatment sources to improve effectiveness of the injected medicament.

BACKGROUND

Infusion pumps and other devices are used regularly for subcutaneous injections of therapeutic fluids, drugs, proteins, and other compounds for humans or animals. Such delivery systems and methods are used also for insulin delivery. A conventional infusion pump is an infusion device specifically adapted for infusing a drug to the subcutaneous tissue using an infusion set connecting the drug reservoir within the pump to a catheter adhered to the skin. The pump and infusion set can be disconnected and reconnected to the catheter leaving only the catheter on the skin when the user desires, for example, before swimming or taking a shower or other activities that might harm the pump or when the pump might disturb the activity. Typically, the infusion set including the catheter is replaced regularly, usually every three days.

Infusion pumps may deliver medicament around the clock. For example, an infusion pump may provide a slow drip of medicament that may be increased by the user or by other input before an event that requires a large amount of medicament. For diabetics, insulin infusion pumps deliver basal insulin around the clock, in addition to a bolus dose of insulin, which may be adjusted by the user, to be delivered by the infusion pump before, during, or immediately after a meal. It is desired that the bolus dose of drug or insulin reaches the circulatory system quickly, and provides an amount of insulin that matches the amount of carbohydrates consumed by the patient. This fast acting delivery to the circulatory system is not required for the basal drip.

It is estimated that a large number of infusion pumps are being used today by hundreds of thousands of diabetics worldwide. Introducing a new pump to the market is a process that may take a few years, and it could take many years to phase out existing pumps. Additionally, diabetic patients who are required to receive several procedures per day to control their blood glucose level will be reluctant to adopt new treatments that will require them to perform additional procedures on top of the procedures they already receive.

When a diabetic patient consumes food, his or her level of glucose rises. Unfortunately, existing subcutaneous injection devices, including infusion pumps, are incapable of quickly matching or preventing the rise of blood glucose. The delay in such matching is also true in case of "rapid-acting" insulins. Some of the reasons for this delay include a lag in the absorption of insulin from the time insulin is injected at the injection site to the time it takes for complex insulin molecules to break down into monomers.

Additionally, since blood glucose levels rise shortly following the meal, the delay in matching insulin to the rising glucose level may cause a post prandial hyperglycemic event (i.e., when the blood glucose level is above normal) to occur. Furthermore, after a certain period of time passes after a meal (e.g., 2-3 hours), the blood glucose level could drop while the insulin concentration in the blood rises followed by the peak of the systemic insulin effect. This may cause a hypoglycemic event (i.e., when the blood glucose level is below normal) to occur. Both hyperglycemic and hypoglycemic events are highly undesirable. Additionally, since local blood perfusion at the insulin injection region, including that of insulin infusion set connected to insulin infusion pump, has large variability, depending on the ambient temperature and other parameters, it induces large variations to the delay of the peak of time profile of the insulin action. Those variations in the insulin peak action period further increase the variability in the blood glucose level.

Additionally, it is known that certain drugs, including insulin, are growth hormones. These drugs, when injected several times at the same location, can cause local cell growth, causing Lipohypertrophy. Using regular infusion sets and infusion pumps, the drug may be infused several times per day, and possibly for several days, at the same location, which could result in Lipohypertrophy. Increasing local blood perfusion at the injection site to promote drug uptake to the circulatory system may reduce the unwanted Lipohypertrophy phenomenon.

Therefore, it is desirable to provide a system and method that provide efficient and rapid uptake of infused drug to the circulatory system when the drug is infused by an infusion pump, that are compatible with existing infusion pumps. In particular, it is desirable to provide a system and method for injection of insulin to the user through an unmodified infusion pump without requiring additional (extra) efforts from the user while using the pump and infusion set. Additionally, it is desirable to provide a system and method that provide treatment only in instances where the pump delivers bolus insulin doses to maintain a normal blood glucose level and prevent or reduce hyperglycemic and hypoglycemic events, and reduce Lipohypertrophy.

SUMMARY

The present disclosure relates to systems, devices, and methods for infusing one or more drugs, substances, and/or chemicals to a user that improve the effectiveness of drug delivery upon infusion of the drug(s) from an insulin pump, that are compatible with existing pumps (e.g. without modifying the pump) and minimize the number of steps required by the user when disconnecting and/or reconnecting the pump from the catheter or infusion set. The systems, devices, and methods may provide an additional treatment to a tissue region where the drug is delivered. In some embodiments, the treatment is utilized to improve the drug delivery process by improving the drug's pharmacokinetic and/or pharmacodynamic profile. The treatment may include, but not limited to, methods and devices described in PCT/

IB2008/051049, PCT/IB2008/051044, and PCT/IB2009/007600, which are incorporated herein by reference. In some embodiments, the treatment may come in various forms, for example, including an analgesic, vasodilator or the like. In some embodiments, the treatment may be any form of treatment that leads to improved vasodilatation of the tissue being injected. To improve the drug's pharmacokinetic and/or pharmacodynamic profile, the treatment may optionally include, but not limited to, exposing the tissue region to energy, radiation, heat, mechanical vibrations, suction, massaging, acoustic stimulation, electrical stimulation, injection of one or more additional substances, or any combination of the above. Each treatment type may optionally have a separate protocol in order to evoke the necessary reaction such as vasodilatation or the like.

In some embodiments, the applied treatment induces vasodilatation through neural stimulation of the tissue around the drug infusion site through the infusion set and infusion pump. The neural stimulation can e induced by thermal stimulation. The human neural response to thermal stimulation includes several mechanism such as the Nociceptive Axon Reflex that induces vasodilatation, among other effects.

In some embodiments, the induced neural response, such as the nociceptive axon reflex, also optionally induces widening of the capillary pores and increasing the capillary wall permeability. This effect is also significant for improving the absorption of the drug through the capillary wall.

In some embodiments, the applied treatment may lead to a reduction in the variability of the drug absorption in the blood or lymph system, and its local and systemic effects. For example, heating the tissue region in the vicinity of the area of drug delivery through an infusion set catheter connecter to an infusion pump, to a preset regulated temperature during and/or after the drug infusion and absorption into the blood may cause local blood perfusion at that region to become more reproducible and the drug absorption process more uniform and reproducible as well. Also, by reducing the delay between drug infusion into the tissue through the infusion set catheter connected to infusion pump, and absorption into the blood system, the variability of drug action induced by the delayed profile can be reduced. In some embodiments, the temperature of the region adjacent to the infusion region through the infusion set catheter connected to infusion pump is regulated for longer periods, but this may require additional energy source capacity and increase weight. Therefore, to minimize the energy source size, the heating period or heating temporal profile should be optimized in relation to the period of the drug infusion and absorption into the blood. In some embodiments in which the treatment utilized is, for example, heat, the drug interaction with the treatment substance or type will be preferably taken into consideration and avoided. In some embodiments, a drug's temperature sensitivity will be accounted for so as to avoid, for example, protein denaturisation. For example, since insulin is a temperature sensitive protein, a treatment protocol, which includes heat, may be limited so as to ensure the efficacy of the delivered drug when it contains insulin. To achieve this, the treatment protocol may control the temperature or the location of the treatment delivery site so as to not damage the drug. For instance, heating some types of insulin above 37° C. may damage the insulin. Accordingly, in some embodiments, the tissue around the infusion site is heated to induce the desired neural response without heating the insulin itself above 37° C. For example, heating the tissue at a distance of 10 mm around the injection site to 38.5° C. provides a significant vasoldilatation without heating the injected insulin above 37° C. It is also possible to heat with a spatial distribution of temperature around the center of the infusion set catheter connected to an infusion pump in a manner such that a region away from the center is heated at a higher temperature while a region closer to the center is heated at a lower temperature.

According to some embodiments of the present disclosure, a system, device, and method for delivering a therapeutic substance to the body of a mammal is provided. For example, the device may includes a reservoir for storing the therapeutic substance; an infusion set including a catheter, a catheter housing for housing the catheter, a proximal connector for connecting to the reservoir, a distal connector for connecting to the catheter housing, and a drug delivery tube connecting the proximal connector and the distal connector; and a pump adapter for securing a pump containing the reservoir and the proximal connector of the infusion set. The pump adapter and the proximal connector of the infusion set include connecting electrical contacts, which may be constructed and arranged such that the electrical contacts are aligned and connected to one another in a single action when the pump and the proximal connector are being secured to the pump adaptor.

In some embodiments, the proximal connector of the infusion set and the reservoir may be constructed and arranged so as to be connected to one another in the same single action when the pump and the proximal connector are being secured to the pump adapter.

According to some embodiments of the present disclosure, the distal connector of the infusion set and the catheter housing include additional connecting electrical contacts, which may be constructed and arranged such that the additional connecting electrical contacts are aligned and connected to one another in a single action when the distal connector and the catheter housing are being connected to one another.

In some embodiments, the device further includes a treatment element for performing a treatment on the mammal. The device may also include a controller for controlling the treatment element. For example, the controller may be configured to active the treatment element based on information regarding the therapeutic substance, which may be stored, for example, with the reservoir containing the therapeutic substance. The device may further include means for determining if the infusion set has been previously used and/or a number of times that the treatment element has been activated. For example, the means may include one or more fuses which is burned each time the treatment element is activated.

According to some embodiments of the present disclosure, the infusion set includes identifying means that uniquely identifies the infusion set. The controller may be configured to execute a treatment protocol based on the information regarding the therapeutic substance.

In some embodiments, the therapeutic substance to be delivered by the device is insulin. The device may further include electronics for sensing pump activation and determining whether the insulin is being delivered to provide basal infusion and bolus infusion. The controller may be configured to activate the treatment element only if the insulin is being delivered to provide bolus infusion.

Details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

For a better understanding of the present disclosure, reference is made to the following description, taken in conjunction with the accompanying drawings, in which like reference characters refer to like parts throughout, and in which.

DETAILED DESCRIPTION

Figure 1:
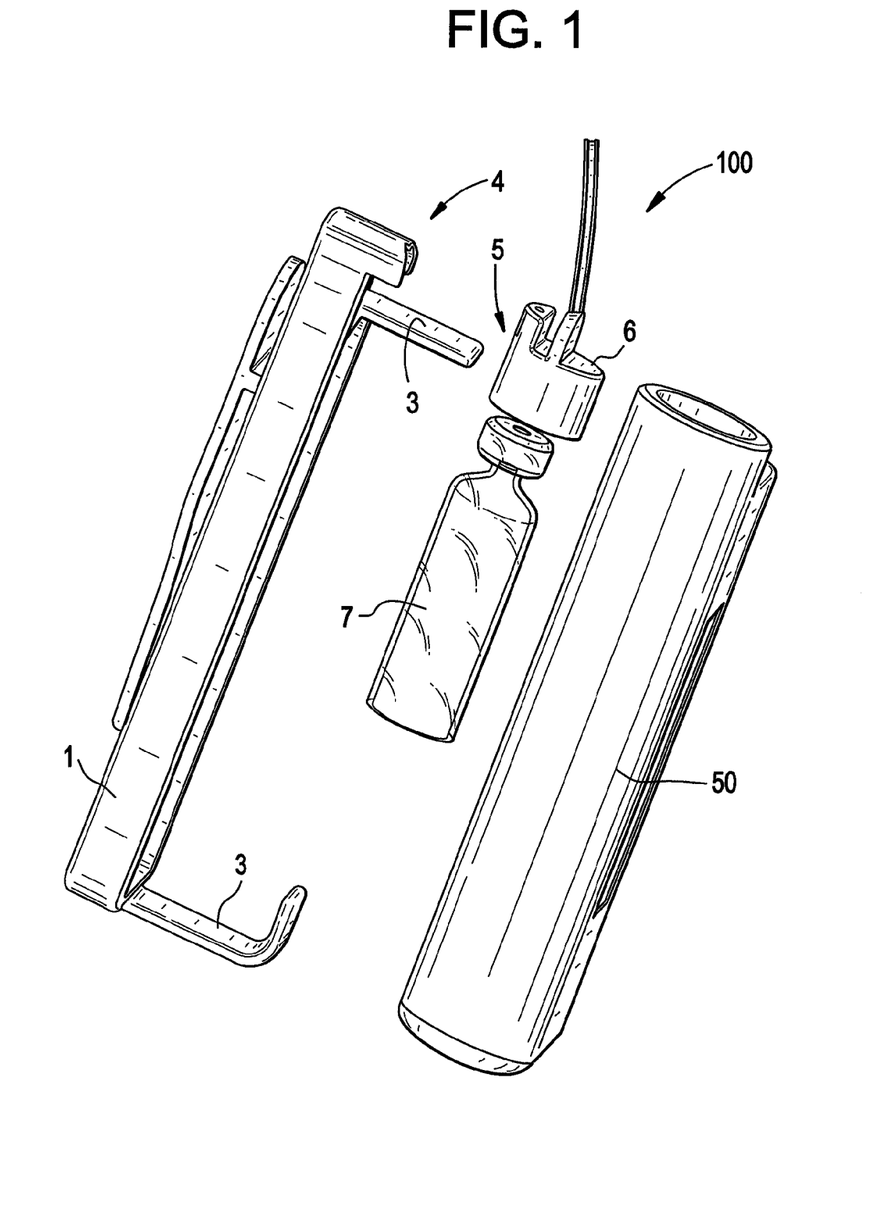
FIG. 1 illustrates an exemplary device for drug delivery according to some embodiments of the present disclosure.

Embodiments of the present disclosure relate to systems, devices and methods for delivering a therapeutic substance to the body of a mammal. FIG. 1 shows an infusion device 100, which includes an infusion pump adapter 1 adapted to be used with, for example, a conventional (unmodified) infusion pump 50. Device 100 also includes an infusion set 8 having an infusion set catheter. In some embodiments, infusion pump adapter 1 is reusable and/or infusion set 8 is disposable. In some embodiments, one or more parts (i.e. including all) of the infusion set 8 is disposable. Infusion pump adapter 1 may include a power source, a controller, one or more sensors for detecting infusion pump activity (not shown), one or more optional LED indicators 20, one or more mechanical fixing elements (e.g. attachment arms 3) for attachment to infusion pump 50, and/or an optional clip to a belt 21. The power source may be rechargeable. Infusion pump adapter 1 may also include electrical contacts 4, which are constructed and arranged to make electrical contact with electrical contacts 5 provided on a proximal connector 6 of infusion set 8 when proximal connector 6 is connected to infusion pump reservoir 7 while infusion pump 50 is secured to infusion pump adapter 1 by mechanical fixing elements 3. In the infusion pump adapter 1 shown in FIG. 1, electrical contacts 4 are provided on a curved surface of infusion pump adapter 1, and electrical contacts 5 of proximal connector 6 are provided on a mating curved surface of connector 6. Infusion pump adapter 1, proximal connector 6, infusion pump reservoir 7, and infusion pump 50 are constructed and arranged such that the connection to pump reservoir 7 and electrical contacts (4 and 5) can be achieved in a single action. For example, infusion pump adapter 1, proximal connector 6, infusion pump reservoir 7, and infusion pump 50 may be constructed and arranged such that as proximal connector 6 and infusion pump 50 are secured to infusion pump adapter 1, the connection between proximal connector 6 and infusion pump reservoir, and the connection(s) between electrical contacts 4 of infusion pump adapter 1 and electrical contacts 5 of proximal connector 6 can be established in a single action.

Figure 2:
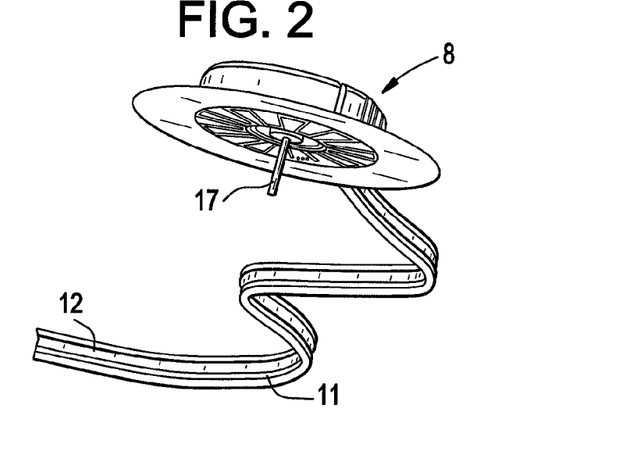
FIG. 2 illustrates an exemplary infusion set according to some embodiments of the present disclosure.
Figure 3:
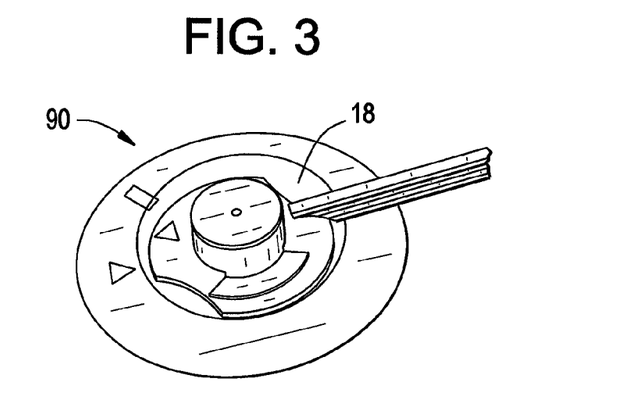
FIG. 3 is a top perspective view of the infusion set shown in FIG. 2.
Figure 4:
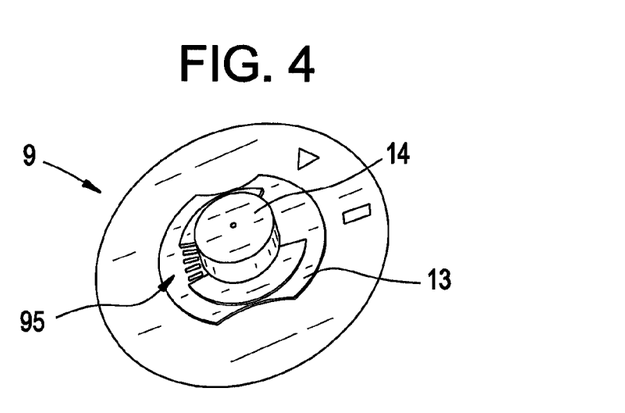
FIG. 4 is a top perspective view of an exemplary catheter housing according to some embodiments of the present disclosure
Figure 5:
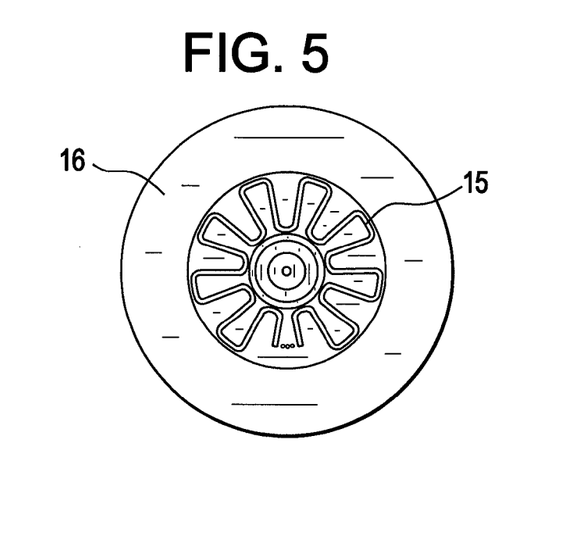
FIG. 5 is a bottom view of the infusion set shown in FIG. 2.
Figure 6:
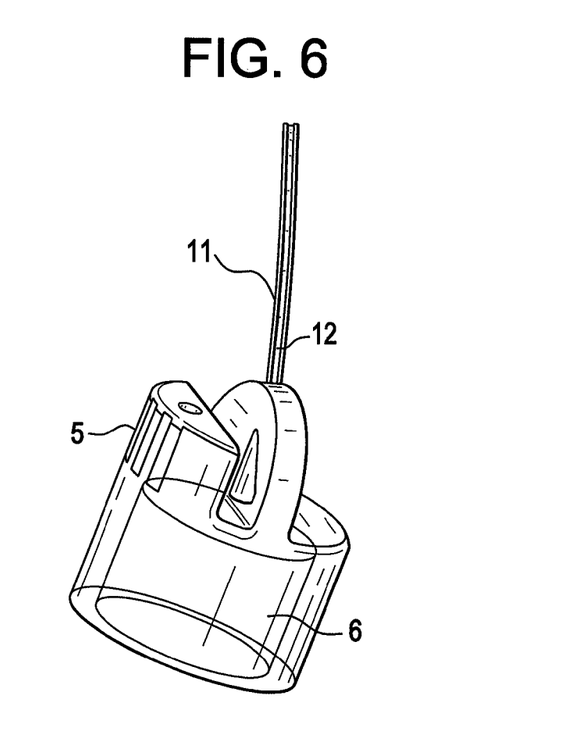
FIG. 6 illustrates an exemplary proximal connector of an infusion set according to some embodiments of the present disclosure.
Figure 7:
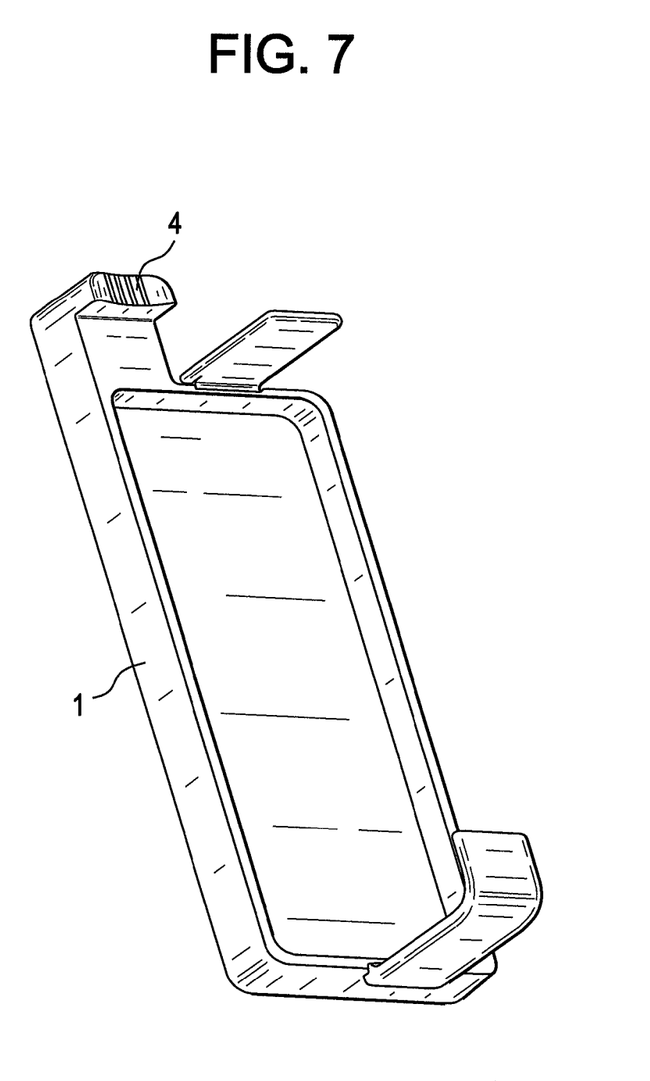
FIG. 7 is a perspective view of an exemplary infusion pump adapter according to some embodiments of the present disclosure.
Figure 8:
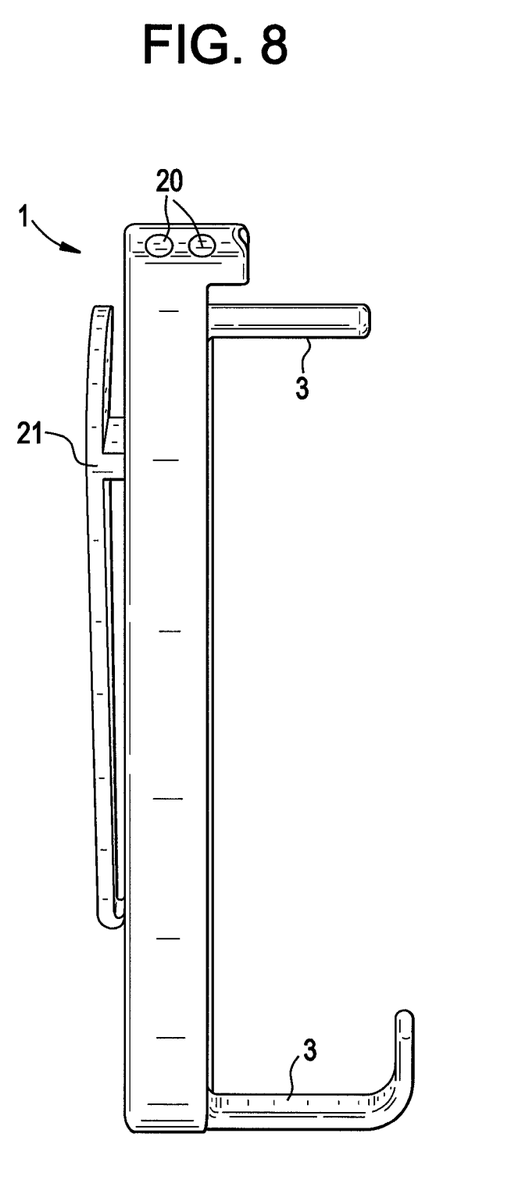
FIG. 8 is a side elevation view of an exemplary infusion pump adapter according to some embodiments of the present disclosure.

Infusion set 8 includes a drug, delivery tube 12 providing a conduit for the fluid, and one or more electrical wires 11 extending along the set. Drug delivery tube 12 and electrical wires 11 may reside in separate casings, which may be attached to or integrated with one another to form a single tube. Infusion set 8 also includes connectors having electrical contacts. Specifically, the connectors of infusion set 8 include a proximal connector 6 having electrical contacts 5, which is adapted to connect to pump reservoir 7 and a distal connector 90, having electrical contacts (not shown), which is adapted to connect to an infusion set catheter 9. Referring to FIGS. 3 and 4, infusion set catheter 9 includes a catheter housing 13 having electrical contacts 95 (for connecting to the electrical contacts of distal connector 90) and a drug input port 14 with a self-sealing feature, one or more treatment elements 15, adhesive layer 16 to secure the catheter to the skin, and a cannula 17 which is inserted subcutaneously into the user in use. A drug path 18 between cannula 17 and drug input port 14 of catheter 9 allows the drug to be delivered from infusion pump reservoir 7, through the infusion set, to the tissue when the catheter is secured to the skin and connected by infusion set 8 to infusion pump 50. Distal connector 90 of the infusion set 8 and catheter housing 13 are constructed and arranged such that when connecting distal connector 90 to catheter housing 13, the electrical contacts of distal connector 90 and electrical contacts 95 of catheter housing 13 are aligned and connected, in a single action, as well as the alignment and connection of drug delivery tube 12 of infusion, set 8 with drug input port 14 of infusion set catheter 9.

Electronics and the controller on infusion pump adapter 1 may be configured to determine whether the drug to be infused requires activation of the treatment in order to achieve improved performance of the drug. In some embodiments, the controller is configured such that the treatment is activated only for the infusions for which the treatment is desired. For infusions of drug where it is not desirable to activate the treatment, the controller does not activate the treatment during infusion of the drug.

To provide the "activation only when appropriate" feature, means can be provided to distinguish between infusion of drugs that require treatment and infusion of drugs which do not require treatment (or if treatment is undesirable). In some embodiments, this can be activated by the user by pressing a button, or perform a different action for different infusion types. For example, the controller may be configured to detect when the pump is used to provide bolus infusion and activate the treatment only with these infusions. Automatic recognition can be achieved, for example, by providing electronics for sensing pump activation and determining whether the drug is being delivered to provide basal infusion and bolus infusion. In some embodiments, the controller can receive information from a user device, for example, for measuring the blood glucose, or other devices used for diabetes treatment, and determine whether the infusion of drug requires treatment activation based on the received information.

Based on the drug information received by the controller (e.g. in the reusable part), the controller may also control various parameters of the treatment and/or apply the treatment according to a predetermined protocol or algorithm. For example, the controller may control temporal and/or spatial parameters of heat treatment (e.g. adjusting a heating rate and/or timing, and/or adjusting the spatial temperature distribution such that the skin temperature and tissue regions around but not close to the catheter tip are at a higher temperature without causing any damage to temperature sensitive drugs).

In some embodiments, infusion set 8 includes identification means, such that infusion pump adapter 1 can identify, for example, whether the infusion set was already used, or how many times the infusion set 8 has been used for heating the injection site. In some embodiments, the infusion set has a serial number, which may be provided, for example, as a unique number embedded in an EPROM chip that identifies the infusion set. In other embodiments, the infusion set may be provided with an RFID chip that uniquely identifies the infusion set. In still other embodiments, the infusion set may be provided with an optical barcode that uniquely identifies the infusion set.

In some embodiments, infusion set 8 has a set of fuse-like conductive elements, which are manufactured in the same process together with the heating element, such as by conductive printing or PCB etching, or other known low-cost manufacturing methods for conductive elements. The fuse-like conductive elements can be produced, for example, by printing a short and narrow conductive element. For each use, infusion pump adapter 1 burns one of the fuse-like conductive elements by applying a short electrical (e.g. high) current signal to that fuse-like conductive element. By this way, the controller can check if all the fuses (fuse-like conductive elements) have been burned to identify whether the infusion set can be used again. This type of mechanism provides additional safety protection such that the infusion set will not be used for too many infusions, which could damage or influence the heating accuracy or the contact to the tissue.

According to some embodiments of the present disclosure, infusion pump adapter 1 and/or infusion set 8 include means for detecting a volume of the infused subcutaneous drug stored in a depot and adjusting the tissue treatment, according to the detected volume. This can be achieved, for example, by adding an electrode to the catheter (which may be disposable), which can be used for electrical impedance measurement, and providing, in infusion pump adapter 1, electronics for use with the controller to support the impedance measurement. Once the drug is infused to the subcutaneous tissue, it alters the impedance measurement result and as it clears from the depot, the impedance measurement returns to the baseline. Thus, by tracking the impedance measurement, the device can detect the clearance of the drug from the subcutaneous depot and the treatment to the tissue can be adjusted accordingly. For example, the treatment can depend on the volume of the drug depot as well as on the velocity by which the drug clears from the depot so that when the depot is cleared, the treatment stops; or if the clearance velocity is low, the treatment can be increased.

In some embodiments, the controller can use the measurements from the electrode to detect leaks of the drug from the infusion set or the catheter, and alert the user of such events.

Although particular embodiments have been disclosed herein in detail, this has been done by way of example and for purposes of illustration only, and is not intended to be limiting. In particular, it is contemplated by the inventors that various substitutions, alterations, and modifications may be made without departing from the spirit and scope of the disclosed embodiments. Other aspects, advantages, and modifications are considered to be within the scope of the disclosed and claimed embodiments, as well as other embodiments disclosed herein. The claims presented hereafter are merely representative of some of the embodiments disclosed herein. Other, presently unclaimed embodiments are also contemplated. The inventors reserve the right to pursue such embodiments in later claims and/or later applications claiming common priority.

What is claimed is:

1. A device for delivering a therapeutic substance to the body of a mammal, comprising:
    a reservoir for storing the therapeutic substance;
    an infusion set comprising:
        a catheter;
        a catheter housing for housing the catheter;
        a proximal connector for connecting to the reservoir;
        a distal connector for connecting to the catheter housing; and
        a drug delivery tube connecting the proximal connector to the distal connector; and
    a pump adapter for securing at least the proximal connector of the infusion set to the reservoir;
    wherein, the pump adapter and the proximal connector of the infusion set comprise connecting electrical contacts, which are constructed and arranged such that the electrical contacts are aligned and connected to one another in a single action when the pump and the proximal connector are being secured to the pump adapter.

2. A device according to claim 1, wherein the proximal connector of the infusion set and the reservoir are constructed and arranged so as to be connected to one another in the same single action when the pump and the proximal connector are being secured to the pump adapter.

3. A device according to claim 1, wherein the distal connector of the infusion set and the catheter housing comprise additional connecting electrical contacts, which are constructed and arranged such that the additional connecting electrical contacts are aligned and connected to one another in another single action when the distal connector and the catheter housing are being connected to one another.

4. A device according to claim 3, wherein the catheter housing comprises a drug input port and the distal connector of the infusion set comprises a drug path, the drug input port and the drug path are constructed and arranged so as to be connected to one another when the distal connector and the catheter housing are being connected to one another.

5. A device according to claim 3, wherein the drug input port of the catheter housing is self-sealing.

6. A device according to claim 1, wherein the catheter housing comprises a treatment element.

7. A device according to claim 1, wherein the infusion set further comprises a treatment element for performing a treatment on the mammal.

8. A device according to claim 7, further comprising a controller for controlling the treatment element.

9. A device according to claim 8, wherein the controller is configured to activate the treatment element based on information regarding the therapeutic substance.

10. A device according to claim 8, further comprising means for determining if the infusion set has been previously used and/or a number of times that the treatment element has been activated.

11. A device according to claim 10, wherein the means comprises one or more fuses which is burned each time the treatment element is activated.

12. A device according to claim 9, wherein the information is stored with the reservoir.

13. A device according to claim 8, wherein the infusion set comprises identifying means that uniquely identifies the infusion set.

14. A device according to claim 9, wherein the controller executes a treatment protocol based on the information regarding the therapeutic substance.

15. A device according to claim 9, wherein the therapeutic substance is insulin, the device further comprises electronics for sensing pump activation and determining whether the insulin is being delivered to provide basal infusion and bolus infusion, the controller activating the treatment element only if the insulin is being delivered to provide bolus infusion.

16. A system for delivering a therapeutic substance to the body of a mammal, comprising:
   a reservoir for storing the therapeutic substance;
   a pump for housing the reservoir and pumping the therapeutic substance stored in the reservoir;
   an infusion set comprising:
      a catheter;
      a catheter housing for housing the catheter;
      a proximal connector for connecting to the reservoir;
      a distal connector for connecting to the catheter housing; and
      a drug delivery tube connecting the proximal connector and the distal connector; and
   a pump adapter, the pump adapter configured to:
      secure the pump and the proximal connector of the infusion set, and
      secure the proximal connector of the infusion set to the reservoir;
   wherein, the pump adapter and the proximal connector of the infusion set comprise connecting electrical contacts, which are constructed and arranged such that the electrical contacts are aligned and connected to one another in a single action when the pump and the proximal connector are being secured to the pump adapter.

17. A system according to claim 16, wherein the proximal connector of the infusion set and the reservoir are constructed and arranged so as to be connected to one another in the same single action when the pump and the proximal connector are being secured to the pump adapter.

18. A system according to claim 16, wherein the distal connector of the infusion set and the catheter housing comprise additional connecting electrical contacts, which are constructed and arranged such that the additional connecting electrical contacts are aligned and connected to one another in another single action when the distal connector and the catheter housing are being connected to one another.

19. A system according to claim 18, wherein the catheter housing comprises a drug input port and the distal connector of the infusion set comprises a drug path, the drug import port and the drug path are constructed and arranged so as to be connected to one another when the distal connector and the catheter housing are being connected to one another.

20. A system according to claim 17, wherein the infusion set further comprises a treatment element for performing treatment on the mammal;
   the system further comprising a controller for controlling the treatment element;
   the controller being configured to activate the treatment element based on information regarding the therapeutic substance.

* * * * *